United States Patent [19]

Bentall

[11] Patent Number: 4,576,172

[45] Date of Patent: Mar. 18, 1986

[54] SWITCHED ELECTRICAL APPARATUS FOR MEDICAL USE

[76] Inventor: Richard H. C. Bentall, The Basement, 7 Penzance Pl., London W11 4PE, Great Britain

[21] Appl. No.: 495,619

[22] Filed: May 18, 1983

[30] Foreign Application Priority Data

May 26, 1982 [GB] United Kingdom ............... 8215296
May 26, 1982 [GB] United Kingdom ............... 8215301

[51] Int. Cl.⁴ ............................................. A61N 1/32
[52] U.S. Cl. .................................... 128/422; 128/804
[58] Field of Search ............ 128/419 P, 419 PC, 421, 128/422, 423 R, 783, 804; 200/50 A, 50 AA

[56] References Cited

U.S. PATENT DOCUMENTS

| 3,158,060 | 11/1964 | Semenoff et al. | |
|---|---|---|---|
| 3,577,121 | 5/1971 | Wing et al. | |
| 3,738,369 | 6/1973 | Adams et al. | 128/419 PG |
| 3,943,918 | 3/1976 | Lewis . | |
| 3,951,154 | 4/1976 | Hartlaub | 128/419 |
| 4,211,230 | 7/1980 | Woltosz | 128/421 X |
| 4,346,715 | 8/1982 | Gammell | 128/804 X |
| 4,431,001 | 2/1984 | Hakansson et al. | 128/421 |
| 4,471,787 | 9/1984 | Bentall | 128/804 |

FOREIGN PATENT DOCUMENTS 310585 10/1973 Austria .
WO80/01045 5/1980 PCT Int'l Appl. .
1049787 11/1966 United Kingdom .

Primary Examiner—Edward M. Coven
Attorney, Agent, or Firm—Steele, Gould & Fried

[57] ABSTRACT

A portable battery powered electrical therapy apparatus for emitting a low power r.f. field to promote wound healing without significant tissue heating, is provided with an improved switch operable once only to switch on the apparatus when it is desired to commence therapy. The apparatus runs continuously until the battery is drained and then the apparatus is disposed of. The electrical circuits, the battery and the switch contacts are mounted in a sealed container, and the switch can be operated without breaking the seal of the container, thus preventing fluids from flowing into the container so as to prevent the formation of an unsterile culture within the container during therapy.

12 Claims, 2 Drawing Figures

SWITCHED ELECTRICAL APPARATUS FOR MEDICAL USE

FIELD OF THE INVENTION

This invention relates to an electrical switch for medical use, particularly but not exclusively for use in a device for applying a high frequency electromagnetic field to living tissue to promote healing thereof.

BACKGROUND TO THE INVENTION

It has been known for many years that improved healing rates can be achieved by applying r.f. electromagnetic fields to wounded tissue. The therapeutic effects were considered to be due to heating of the tissue by the field and prior therapy apparatus has been configured to produce r.f. energy levels for tissue heating either on the surface or deep into the tissue. This heating technique is known as diathermy. It is known to pulse the field produced by diathermy apparatus. A specific example of the heating effects achieved with a pulsed field diathermy apparatus is given in "A Trial Involving the Use of Pulsed Electromagnetic Therapy on Children Undergoing Orchidopexy" R. H. C. Bentall and H. B. Eckstein, Zeitschrift fur Kinderchirurgie und Grenzgebiete p 380–398 November 1975.

Heretofore the pulsed electromagnetic field has been produced by hospital or laboratory based equipment comprising an electrical signal generator which feeds an induction coil mounted on a stand, positioned adjacent an area of a patient to be treated. This apparatus is bulky and has the disadvantage that a patient cannot be treated on a continuous intensive basis without being hospitalised.

More recently, it has been appreciated that the therapy produced by an applied r.f. field is not characterised solely in terms of the tissue heating effect of the field. A discussion of this subject is given in my paper entitled "Healing by Electromagnetism-Fact or Fiction" New Scientist Apr. 22, 1976.

I have devised a lower powered portable apparatus for producing the electromagnetic field, suitable for being attached to a patient, to produce therapy at power levels which do not produce any significant tissue heating. Such portable apparatus is described in my U.S. Pat. No. 4,429,698 entitled "Treatment Inductors" and corresponding published U.K. Patent Application No. 2027594.

This portable apparatus comprises a battery driven r.f. oscillator and an antenna which is flexible to overlie an area of tissue to be treated. The apparatus thus can be attached to the patient and left running on a substantially continuous basis. The portable apparatus produces an electromagnetic field typically in the frequency range 3–30 MHz, the particular r.f. frequency not being of great significance as to the efficacy of the therapy. The r.f. field is pulsed in a manner to maximise the therapeutic effect. The field is of a strength which does not produce any significant tissue heating. The portable device thus operates at much lower power levels than bulky diathermy apparatus, typically to produce r.f. field of less than 100 mW cm$^{-2}$ as measured at the skin of the tissue, and utilising a fundamentally different premise as to the manner in which a r.f. field may be utilised to effect treatment, namely that the field does not have to produce tissue heating in order to produce an improved healing rate.

SUMMARY OF THE INVENTION

It is an object of the invention to provide a low power therapy device of the kind described in my U.S. Patent aforesaid, which can be manufactured for use as a portable device with its own power source such as a battery, which can be attached to a patient and rendered operative when it is desired to commence therapy. Thus, it is desirable to include a switch so that the device may be switched on at the time it is desired to commence therapy, but the provision of a conventional switch introduces significant problems.

Firstly, conventional switches are bidirectional devices which can be switched on and off, so with a conventional switch there is a risk that the device may be spuriously switched off during a period in which it is assumed that therapy is being performed by the device.

Secondly, the mechanical arrangement of electrical contacts in conventional switches are difficult to maintain in a clean condition. During therapy, which may last for several weeks, wound fluids may flow into the switch structure which may render the switch ineffective. Moreover, since the interior structure of the switch cannot be easily cleaned, the fluids when in the switch can provide a suitable culture for germs to multiply, rendering the device unsterile and substantially degrading the therapeutic effects of the applied r.f. field.

In an embodiment of the present invention, a therapy device is provided with a switch which is operative from an initial non-conductive condition to a conductive condition, but which is not thereafter operative to a non-conductive condition. The switch has its contacts mounted in a sealed container together with the power source and electrical circuits of the therapy device, and the switch can be operated to its conductive condition without breaking open the seal of the container. Thus, when the device is activated, it cannot be thereafter deactivated and continues to emit the therapeutic field until its power source becomes drained. Since the seal of the container is not broken when the device is activated, wound fluids are not able to flow into the switch contacts or the electrical circuits, and so the likelihood of an unsterile condition developing is materially reduced.

In the embodiment of the invention described hereinafter, the switch includes a grippable portion which is pulled to activate the apparatus, and which then releases from the device. The removal of the grippable portion provides a visual indication that the device is activated.

Further features and advantages of the invention will become apparent from the following description of an embodiment thereof given with reference to the accompanying drawings.

DETAILED DESCRIPTION OF THE PREFERRED EMBODIMENTS

Figure 1:
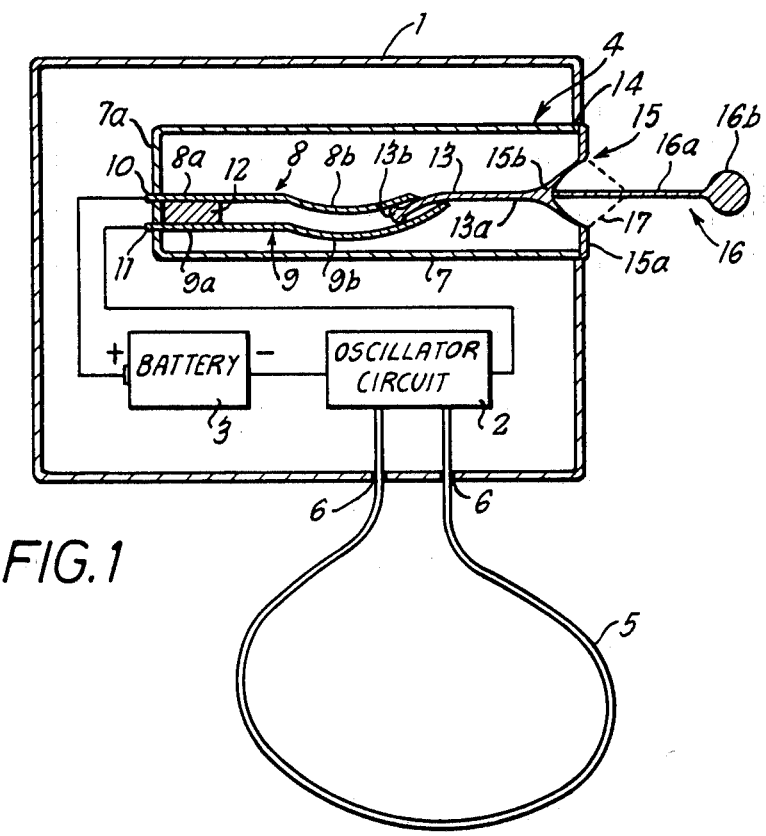
FIG. 1 is a schematic illustration partially in section of a battery driven portable therapy apparatus incorporating a once only action switch.

The therapy device shown in FIG. 1 is a portable device for attachment to a patient, and is adapted to emit a low strength pulsed electromagnetic field for promoting healing of wounds, without any significant tissue heating.

The therapy device comprises a closed plastics container 1 in which is disposed a r.f. oscillator circuit 2 driven by an alkali battery 3 under the control of a switch 4. The oscillator circuit has an antenna which in this example comprises a loop of coaxial cable 5 that passes through sealed apertures 6 in the housing. When the device is switched on the antenna is fed a pulsed r.f. signal of a frequency typically in the range of 3–30 MHz, for example 27.12 MHz, an allowed frequency for medical uses. The antenna typically defines a loop of 30 cm circumference and the dimensions of the container 1 are typically 3×2×2 cm. The device is thus portable and in use is taped or similarly attached to a patient with the flexible coaxial cable antenna 5 being conformed to an area of tissue to be treated. The tissue area may additionally be provided with a wound dressing (not shown). The device operates at power levels which do not produce a significant tissue heating, typically 100 mW cm$^{-2}$ or less. The r.f. emission is pulsed for example at 0.1 Hz to 10,000 Hz. As is discussed in my article in New Scientist, mentioned above, this r.f. emission promotes healing of wounded tissue.

The oscillator circuit 2, the battery 3 and switch 4 are sealed within the container 1 during manufacture of the device. The switch 4 is initially in a non-conductive condition. when it is desired to commence therapy, the switch is operated to its conductive condition thereby energising the oscillator, and the device emits the pulsed r.f. field on a continuous basis until the battery discharges. The device is then disposed of.

Referring in more detail to the switch 4, it comprises a switch housing 7 typically made of plastics material as a cylinder with an integral end closure 7a. Within the housing 7 is arranged current control means, which will be described in detail. First and second electrical contacts comprising sprung metal finger members 8, 9 are mounted in apertures 10, 11 in the end closure 7a. The finger members 8, 9 are conveniently formed by stamping from sheet metal and each have a straight shank portion 8a, 9a and a curved end portion 8b, 9b. The shank portions 8a, 9a are held spaced apart by an electrically insulating block 12. The curved end portions 8b, 9b are held spaced apart by a removable, flexible, elongate electrically insulating member 13.

When the member 13 is removed from between the contacts 8 and 9, as will be described hereinafter in detail, the sprung nature of the contacts is such that they are urged into engagement with one another and the curved portions 8b, 9b are of such a shape that their most adjacent curved faces engage in intimate contact over substantially their entire surface area, thus establishing the conductive condition of the switch.

The cylindrical switch housing 4 is sealingly mounted in an aperture 14 in the container 1. The housing 4 is closed by an end cap 15 comprising a rigid annular wall portion 15a to which is attached (or integrally formed) a flexible wall portion comprising a re-entrant conical plastics mouldng 15b. The member 13 has an end 13a which is formed integrally with the conical portion 15b whereas the portion of member 13 between the contacts 8, 9 is provided with a ball shaped termination 13b of a diameter greater than the thickness of the rest of the member 13 between the contacts. A flexible plastics grippable portion 16 is attached to or integrally formed with the flexible conical portion 15b on the outside of the housing 1. The grippable portion comprises a stem 16a and a handle 16b.

To operate the switch, the handle 16b is pulled manually and outwardly of the container 1. The conical portion 15b of the flexible end wall has two stable positions, one of which is as shown in the drawing i.e. in its re-entrant configuration, and the other position is protruding outwardly of the container 1 as shown schematically by hatched line 17. The conical portion 15b thus assumes the position 17. Consequently the member 13 is pulled longitudinally from between the contacts 8, 9 allowing them to engage and establish a conductive path. The therapy device is thus switched on. The ball shaped termination 13b reduces the contact area between the member 13 and the contacts 8, 9 thereby reducing frictional resistance to the removal of the member from the contacts.

The member 13 cannot be re-inserted between the contacts 8, 9 by pushing the flexible wall portion 15b inwardly. The member 13 is flexible and possesses insufficient rigidity in longitudinal compression to pry open the contacts 8, 9. Also, the ends of the contacts 8, 9 are of a configuration to deflect the member 13 away from the region where they mate. Thus, once the switch 4 is switched on, it cannot be subsequently switched off.

The connection between the stem 16a and the conical portion of 15b is sufficiently strong to enable the member 13 to be withdrawn from between the contacts, as just described. However, this connection is designed to fail when stressed by further pulling on the handle 16b, so that the grippable portion can be removed when the conical portion 15b assumes the position 17. The removal of the grippable portion 16 serves as a positive visual indication that the switch has been operated to its conductive condition. The strength of the joint between the wall portions 15a, 15b is sufficiently strong to withstand the removal of the portion 16, so that at all times the container 1 remains sealed.

The therapy device has the advantage that because the container remains sealed at all times it does not constitute a vessel which could harbour germs when on a patient. If the container was broken open when the switch was operated, fluids might enter the container which would then constitute a suitable environment for germs to multiply, and it would be difficult to clean. It is envisaged that the device will be packaged in a sterile condition in a disposable container, which is disposed of at the time the device is switched on and provided on the patient to provide therapy.

Figure 2:
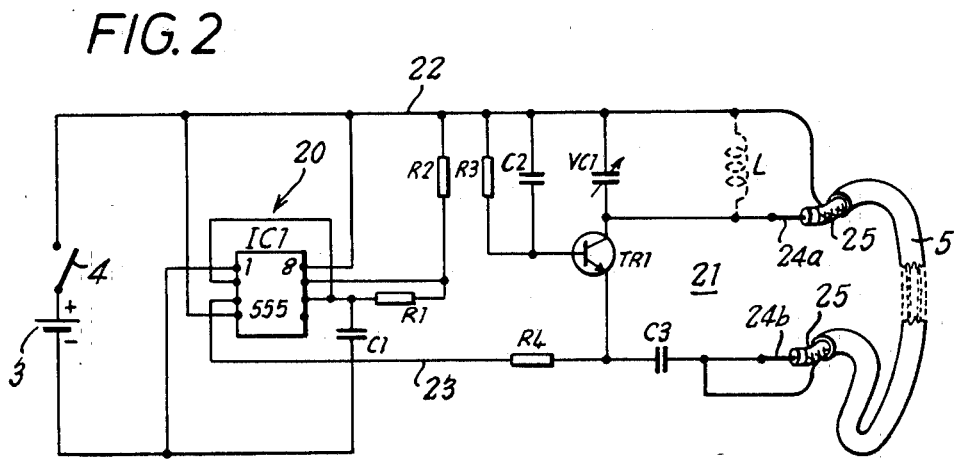
FIG. 2 is a detailed circuit diagram of the oscillator and antenna arrangement shown in FIG. 1.

Referring now to FIG. 2, the oscillator circuit 2 and its connection to the antenna 5, is shown in more detail. The circuit 2 comprises an r.f. oscillator 20 arranged to operate nominally at the allowed medical frequency of 27.12 MHz. The output of the oscillator 20 is pulsed by means of a pulse generator 21 and the resulting r.f. pulses are nominally of 100 μs duration, produced once every 1000 μs.

The r.f. oscillator 21 is driven from d.c. rails 22, 23. The d.c. rail 22 is connected directly to the positive terminal of the battery 3 via the switch 4. The rail 23 is connected to the negative terminal of the battery 3 under the control of the pulse generator 20.

The pulse generator 20 comprises a CMOS type "555" multivibrator ICI connected as shown. Resistors R1, R2 and capacitor C1 define the pulse repetition rate and the mark to space ratio for the multivibrator. In this example, ICI produces rectangular output pulses of 10 μs once every 100 μs. The device ICI is used as a switch to connect the rail 23 to the negative terminal of the battery 3 for the duration of the 10 μs pulses. Accordingly, the r.f. oscillator 21 energises the antenna 2 for the duration of the 10 μs pulses.

The inductance presented by the coaxial cable of the antenna 2 is used as a frequency determining component for the oscillator 21. The coaxial cable of the antenna 5 has its central conductor 24 and screen 25 connected as shown and the cable presents an inductance L which can be represented as shown in FIG. 2. The inductance L is connected in parallel with a variable capacitor VC1 which is adjusted to cause resonance in the parallel LC circuit. It will be appreciated that the impedance presented by the length of coaxial cable will depend upon the exact length thereof utilised and upon the particular type of cable used, and the variable capacitor VC1 allows the circuit to be matched to a particular piece of coaxial cable.

In an alternative arrangement the connections of the ends 24a, 24b of the inner conductor are changed over from the arrangement shown in FIG. 2, such that the end 24a is connected to the capacitor C3 and the end 24b is connected to the collector of transistor TR1. In this way, the individual inductances of the coil and sheath conductors are connected in an additive sense so as to maximize the inductance presented to the oscillator circuit for a given length of antenna.

A transistor TR1 maintains the r.f. resonance, the transistor receiving a base bias potential from the positive rail 22 through resistor R3. It has been found empirically that capacitor C2 promotes and stabilises oscillation in the oscillator circuit 21. A capacitor C3 prevents a d.c. short circuit between the collector and emitter of transistor TR1 through the central conductor 9. Resistor R4 controls the r.f. power emission of the device and hence the rate at which the battery is drained.

A feature of the circuit just described is that the r.f. oscillator 21 is only connected to receive power from the battery 3 for the 10 μs pulse periods defined by the pulse generator 20. For the intervening periods, the r.f. oscillator 21, does not receive or dissipate battery power, which maximises battery life and hence the period for which the device can provide effective therapy. The periodicity and mark to space ratio for the pulsing can be varied and is selected in a manner to maximise the effectiveness of the treatment. However, it has been found that in practice, the actual value of mark to space ratio and periodicity is not critical and can be varied from the aforesaid nominal values without substantial variation in the effectiveness of therapy.

The therapy device herein described is suitable for use as a disposable unit. The device is switched on, arranged on a patient so as to provide therapy and when the battery is expended, the entire device is thrown away.

The device in use produces a r.f. field with a peak power level at the patient's skin of the order of 100 mW cm$^{-2}$ or less, and the r.f. field does not produce any significant heating of the patient's tissue.

The particular r.f. frequency of 27.12 MHz described herein is given by way of example, and effective therapy can be produced over a large frequency range, for example 3–30 MHz. It will be appreciated that the circuit described herein can be readily modified to operate at different frequencies and pulse repetition rates by alteration of the component values.

What is claimed is:

1. Switched electrical apparatus for medical use, comprising:
    a closed sealed container;
    an electrical power source disposed in the container;
    an electrical circuit disposed in the container for being powered by the source;
    an electrical switch including first and second electrical contacts;
    means urging said contacts towards one another to establish an electrically conductive condition therebetween;
    an elongate flexible electrically insulating member between the contacts and holding them apart to establish a non-conductive condition therebetween, said member having an end exteriorly of the contacts for being pulled longitudinally to remove the member from between the contacts to allow them to engage one another and establish said conductive condition; and,
    a flexible wall region in said sealed container to which said end of the member is coupled so that by pulling said wall region outwardly of the container said member is removed from between said contacts, said member possessing insufficient longitudinal rigidity in longitudinal compression that upon urging said wall region inwardly of the container toward said contacts, after removal of said member from between said contacts, the member cannot be re-inserted between the contacts, whereby said conductive condition can be established without breaking the seal of the container, and cannot thereafter be interrupted.

2. Apparatus according to claim 1, including a grippable portion attached to said flexible wall region exteriorly of the container, for facilitating said outward pulling of said flexible wall region.

3. Apparatus according to claim 2, wherein the grippable portion is releasably coupled to the flexible wall region such that the grippable portion will release upon pulling thereof subsequent to removal of the flexible insulating member from between said contacts, whereby to provide a visual indication of operation of the switch.

4. Switched electrical apparatus for medical use, comprising:
    an electrical circuit, including r.f. oscillator means, a pulse generator connected to pulse the output of the r.f. oscillator means to provide trains of pulses of r.f. energy and an antenna, the antenna providing an inductance comprising a frequency determining component of the r.f. oscillator means;
    an electrical power source;
    an electrical switch including current control means operable from an initial non-conductive condition to a conductive condition to supply electrical power from said source to said circuit, the control means being arranged to prevent subsequent operation thereof from said conductive condition to a non-conductive condition;
    a closed sealed container in which the power source, the electrical circuit and the control means are disposed, the antenna sealably protruding from the sealed container, the r.f. oscillator means and the antenna being arranged to cooperate to propagate electromagnetic energy for promoting healing of living tissue; and,
    means for operating the control means to said conductive condition from the exterior of the container and without breaking the seal of the container.

5. Apparatus according to claim 4, wherein said pulse generator is arranged to connect said r.f. oscillator means to the power source only for periods during which said pulses of r.f. energy are produced.

6. Apparatus according to claim 4, wherein said pulse generator comprises a multivibrator.

7. Apparatus according to claim 4, wherein said oscillator includes a time constant circuit including a variable capacitor and said inductance.

8. Apparatus according to claim 4, wherein said antenna comprises a single loop of coaxial cable, the coaxial cable comprising a central conductor and a sheath conductor, the inductance presented to the r.f. oscillator being the inductance between said conductors.

9. A device according to claim 4, further comprising a closed sealed container within which the oscillator circuit, the battery and the switch means are disposed; and, said antenna comprises a single loop of coaxial cable sealably protruding from the sealed container.

10. A device according to clam 4, wherein said battery, oscillator and antenna have operational power levels selected such that said antenna emits, in use, a r.f. field of the order of less than 100 mW cm$^{-2}$ measured at the skin of the patient.

11. A device according to claim 4, wherein said r.f. oscillator operates at a frequency in the range of 3–30 MHz.

12. A device according to claim 4, wherein said r.f. oscillator operates at a nominal frequency of 27.12 MHz and the pulse generator energizes the r.f. oscillator to produce r.f. pulses of 100 $\mu$sec duration every 1,000 $\mu$sec.

* * * * *